United States Patent [19]
Li et al.

[11] Patent Number: 5,270,192
[45] Date of Patent: Dec. 14, 1993

[54] BIOLOGICAL ARTIFICIAL LIVER

[75] Inventors: Albert Pak-Hung Li; Timothy D. Whitehead; Dale J. Beck; George E. Barker, all of St. Louis, Mo.

[73] Assignee: Monsanto Company, St. Louis, Mo.

[21] Appl. No.: 832,461

[22] Filed: Feb. 7, 1991

[51] Int. Cl.$^5$ .................... C12N 11/00; C12M 3/00
[52] U.S. Cl. ................... 435/174; 435/176; 435/240.23; 435/284; 435/285; 604/4
[58] Field of Search ............... 435/1, 240.1, 240.23, 435/283, 171, 176, 284, 286, 287, 299, 310, 311; 604/4-6; 623/66

[56] References Cited

U.S. PATENT DOCUMENTS

| | | | |
|---|---|---|---|
| 3,734,851 | 5/1973 | Matsumura | 435/284 |
| 4,220,725 | 9/1980 | Knazek et al. | 435/285 |
| 4,241,187 | 12/1980 | White | 435/284 |
| 4,242,459 | 12/1980 | Chick et al. | 435/284 |
| 4,242,460 | 12/1980 | Chick et al. | 435/283 |
| 4,330,528 | 5/1982 | Ruhenstroth-Bauer et al. | 424/101 |
| 4,391,909 | 7/1983 | Lim | 435/178 |
| 4,833,083 | 5/1989 | Saxena | 435/284 |
| 4,853,324 | 8/1989 | Viles et al. | 435/283 |
| 4,925,555 | 5/1990 | Spielberg | 210/321.83 |
| 4,963,489 | 10/1990 | Naughton et al. | 435/1 |
| 5,043,260 | 8/1991 | Jauregui | 435/284 |

FOREIGN PATENT DOCUMENTS

| | | |
|---|---|---|
| 0079781 | 5/1983 | European Pat. Off. |
| 0402272 | 12/1990 | European Pat. Off. |
| 3837226 | 5/1989 | Fed. Rep. of Germany |
| 1260022 | 11/1986 | Japan |

OTHER PUBLICATIONS

*Tibtech* vol. 8, 1990, Elsevier, UK. pp. 204–209, D. Looby & B. Griffiths 'Immobilixation of Animal Cells in Porous Carrier Culture'.
Database Wpil Section Ch. Week 8513, Derwent Publications Ltd., London, GB; Class A96, AN 85-080082 & SU,A,1 113 131 (Riga Med. Inst.) Sep. 15, 1984.
*NTIS Tech Notes* Sep. 1990 Springfield, Va. US p. 786, XP000162601.
*PT Procestechniek* vol. 46, No. 12, Dec. 1991, Rijswijk NL pp. 32–35 'Bioreactoren bevorderen welzijn van mens en muis'.
Wolf and Munkelt, Trans. Amer. Soc. Artif. Int. Organs, vol. 21, 1975, pp. 16–27.
Demetriou et al., Ann. Surg., Sep. 1986, pp. 259–271.
Saito et al., Trans. Am. Soc. Artif. Intern. Org., 1987, 33:459–462.
Cai et al., Artif. Organs, 12:388–393, 1988.
Sun et al., Trans. Am. Soc. Artif. Intern. Org., 32:39–41, 1986.
Kawanishi et al., 1988, Trans. Am. Soc. Artif. Org., 34:250–254.
Miura et al., 1986, Art. Org., 10:460–465.
Schindhelm, 1989, Art. Org. 13:21–27.
Cima et al., 1991, Biotech. Bioeng., 38:145–158.
Stieber et al., 1988 ASAIO Transactions, 34:959–964.
Spier and Whiteside, 1976, Biotech. Bioeng., 18:649–657.
Demetriou et al., 1986, Science, pp. 1190–1192, vol. 233.
Wohler et al., 1972, Exp. Cell Res., 74:571–573.
Takahashi et al., Dig. Dis. Sc., 1991, 36:1327–1332 and 1334–1340.
Koide et al., 1990, Exp. Cell Res., 186:227–235.
Gerlach et al., 1990, Int. J. Artif. Org., 13:436–441, (Abstract Only), Chemical Abstract No. CA114(24):235021u.
Gerlach et al., 1990, Artif. Org., 14:328–333, (Abstract Only), Chemical Abstract No. CA114(6):49520f.
Hamada, 1990, Kanzo, 31:669–677, (Abstract Only), Chemical Abstract No. CA113(24):218153a.

(List continued on next page.)

Primary Examiner—Michael G. Wityshyn
Assistant Examiner—William H. Beisner
Attorney, Agent, or Firm—Dennis A. Bennett

[57] ABSTRACT

Disclosed is a hepatocyte bioreactor or bioartificial liver which comprises a containment vessel having a perfusion inlet and a perfusion outlet; a matrix within the containment vessel so as to entrap hepatocyte aggregates within the containment vessel while allowing perfusion of the matrix. The invention is useful as an artificial liver.

24 Claims, 7 Drawing Sheets

OTHER PUBLICATIONS

Arnaout et al., (Dementriou group), 1990, J. Surg. Res., 48:379–382, (Abstract Only), Chemical Abstract No. CA113(12):103349b.

Takabatake, H., Koide, N., and Tsuji, T., "Artificial Organs" 15:474–480 (1991).

Japanese Journal Article (May 4, 1989) (No English Translation).

Lie et al. "Successful Treatment of Hepatic Coma" Res Exp. Med. vol. 185 (1985) pp. 483–494.

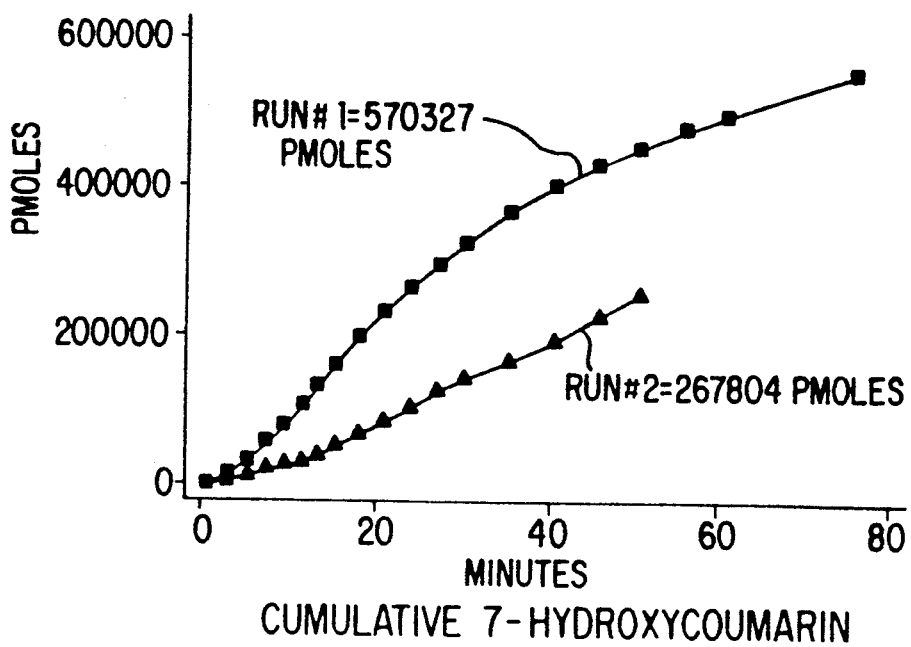
FIG. 6 — CUMULATIVE 7-HYDROXYCOUMARIN
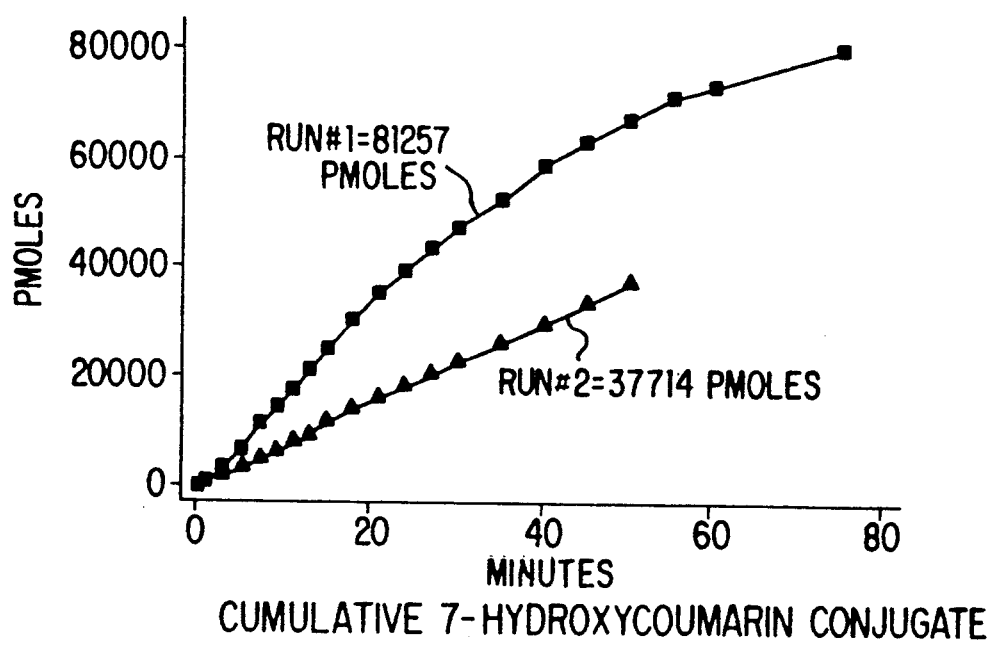
FIG. 7 — CUMULATIVE 7-HYDROXYCOUMARIN CONJUGATE

BIOLOGICAL ARTIFICIAL LIVER

BACKGROUND OF THE INVENTION

1. Field of the Invention

This invention relates to an artificial organ and, more particularly to a liver bioreactor for hepatocyte culturing and use thereof.

2. Related Art

If an effective hepatic assist system existed, it could serve as a bridge to transplantation. Most of the patients waiting for a liver transplantation have chronic liver insufficiency but are not in hepatic coma shock. Various hepatic-assist systems have been used to salvage patients with acute liver insufficiency. Most attempts have been disappointing.

During the past decade, methodologies involving the use of membrane plasma separation techniques have been introduced into the field of hepatic support. Conventional methods, such as hemoperfusion hemofiltration, and dialysis have been improved. However, the application of the most up to date hepatic assist techniques has not improved the survival rate of patients with acute hepatic failure. For the most part, this may be attributed to our limited understanding of the pathology of hepatic failure.

On the other hand, with improvements in immunology and surgical techniques, liver transplantation has become an established therapeutic modality for the fatal liver diseases. It must still be recognized, however, that the regenerative capacity of the liver is almost unlimited. Whether the hepatic injury be viral, toxic, or surgical in origin, the liver usually recovers significant function to be able to sustain life within a couple of weeks, except for cases of fulminant hepatic failure (FHF), where hepatic regeneration is neither rapid nor sufficient enough to keep the individual alive, and end-stage cirrhosis, where hepatic regeneration cannot occur. Takahashi, T., et al., "Artificial liver state of the art", in Digestive Diseases and sciences, Vol. 36, No. 9 (September 1991). Pg. 1327-1340.

For these reasons the desirability of an artificial liver is well appreciated in the art. (JAUREGUI, H. O., et al., "Hybrid Artificial Liver", in Szycher, N. (Ed.), *Biocompatible Polymers, Metals, and Other Composites* (Lancaster, Pa., Technomic Pub.) 1983, Pg. 907-928; Matsumura U.S. Pat. No. 3,734,851.

Several devices which perform the function of the liver have been proposed. Haggar, et al., "Neonatal Hepatocyte Culture on Artificial Capillaries. A Model for Drug Metabolism and the Artificial Liver", ASAIO J. 6:26-35 (January/March 1983), Jauregui, H. O., et al., "Adult Rat Hepatocyte Cultures as the Cellular Component of an Artificial Hybrid Liver", and Paul, J. (Ed.), *Biomaterials in Artificial Organs*, (MacMillan) 1983, Pg. 130-140, describes experiments in which hepatocyte (healthy liver cells) were grown on external surfaces of and into walls of hollow, semipermeable fibers in a cartridge. The later reference suggests treating the fibers with collagen prior to seeding with hepatocyte to improve attachment. U.S. Pat. No. 5,043,260 to Jauregu discloses a perfusion device to grow and maintain hepatocyte. It includes a porous membrane to separate a perfusion compartment from a hepatocyte compartment and employs oligosaccharide lectin recognition linkage to attach hepatocyte to a biopolymer support member in the hepatocyte compartment. Demetriou, et al., "New Method of Hepatocyte Transplantation and Extracorporeal Liver Support" *Ann. Surg.*, Sep. pg. 259-271;1986 shows a technique that allows hepatocyte attachment on collagen coated microcarriers which is placed in a chromatography column which is then perfused.

EP Application 9040158 discloses using a cell-culturing substrate to cause adhesion between the hepatocytes and a synthetic high molecular membrane layer. Lie, et al., "Successful Treatment at Hepatocyte Coma by a New Artificial Liver Device in the Pig" Res. Exp. Med (1985) 185, 483-492 teaches using liver pieces or cubes held by a porous membrane in a perfusion chamber.

Wolf, F. W., and Munkelt, B. E., "Bilirubin Conjugation by an Artificial Liver Composed of Cultured Cells and a Synthetic Capillaries," Vol. 21 *Trans. Amer. Soc. Artif. Int. Organs,* 1975, Pg. 16-23, describes experiments in which rat hepatoma (tumorous liver) cells were provided in the regions between hollow semipermeable fibers and a cartridge and blood was passed through these fibers and treated by the hepatoma cells. In such hollow fiber devices, the fibers are used to isolate these cells from the patient's immune defense system and have pore sizes so as to permit transfer of toxic substances. Cai, Z., et al., "Microencapsulate Hepatocyte for Bio-Artificial Liver Support" Artif. Organs, 12:388-393,1988 teaches encapsulating hepatocytes within alginate-polylysine membranes and serve as a liver support system.

SUMMARY OF THE INVENTION

The invention is a hepatocyte bioreactor or bioartificial liver which comprises a containment vessel having a perfusion inlet means and a perfusion outlet means; a matrix within said containment vessel so as to entrap hepatocyte aggregates within said containment vessel while allowing perfusion of said matrix.

It is an object of the present invention to provide a hepatocyte bioreactor and a method for making same.

It is still another object of the present invention to provide an apparatus and method for treating patients in need of liver support.

It is another object of the present invention to provide an apparatus and method for production of metabolites and other liver cell products.

It is still another object of the present invention to provide an apparatus for studying chemical interaction with hepatocytes.

It is an advantage of the present invention to be able to increase hepatocyte concentration while maintaining viability and liver cell differentiation as compared to the prior art by culturing the hepatocytes as cell aggregates with three-dimensional cell-cell contact.

It is still another advantage of the present invention to be able to have direct and controllable hepatocyte contact with the desired medium.

It is yet another advantage of the present invention to provide an extracorporeal liver support for human treatment which can use non-human hepatocytes. The potential immune response of the patient to the nonhuman hepatocytes is minimized by purposely avoiding contact between the hepatocytes and the patient's blood cells.

It is yet another advantage that the present invention can be scaled to accommodate the quantity of hepatocytes required.

Other objects and advantages of the invention will be apparent from consideration of the following description in conjunction with the appended drawings.

to FIG. 6 shows metabolism of 7-etoxycoumarin by the Hepatocyte Bioreactor to 7-hydroxycoumarin. Runs 1 and 2 were performed at the first and the 6th hrs. After hepatectomy and the connection of the ahepatic animal to the bioreactor.

FIG. 7 shows metabolism of 7-etoxycoumarin by the Hepatocyte Bioreactor to conjugate. Runs 1 and 2 were performed at the first and the 6th hrs. After hepatectomy and the connection of the ahepatic animal to the bioreactor.

Figure 8:
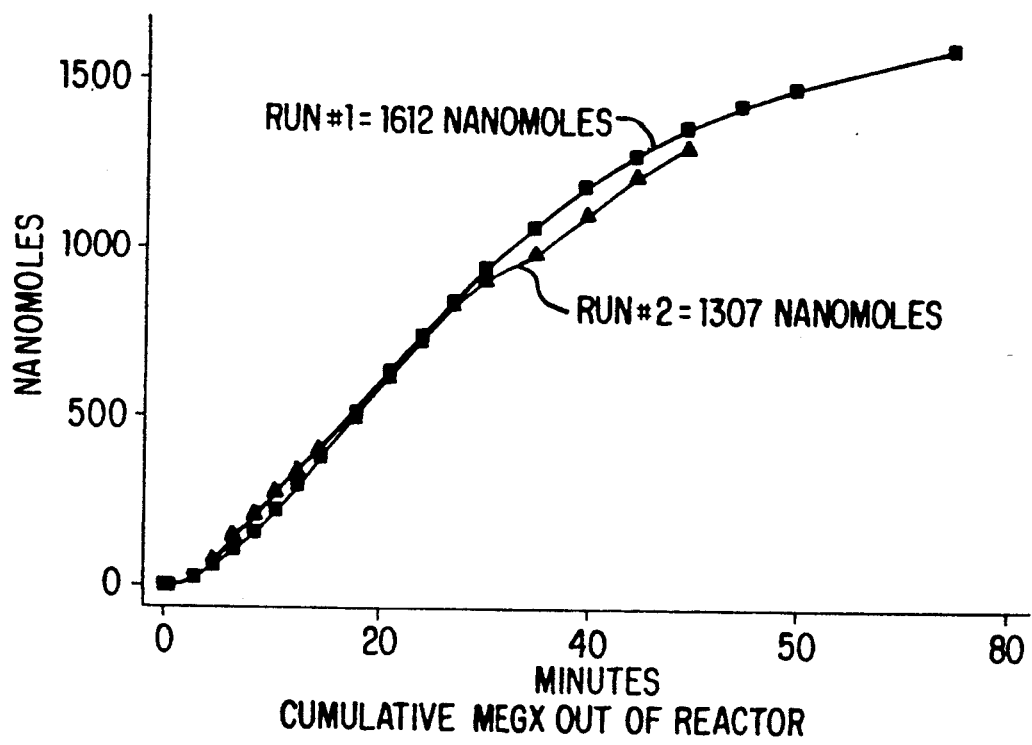

FIG. 8 shows metabolism of lidocaine hydrochloride by the Hepatocyte Bioreactor to monoethylglycinexylide.

DESCRIPTION OF THE PREFERRED EMBODIMENT(S)

Figure 1:
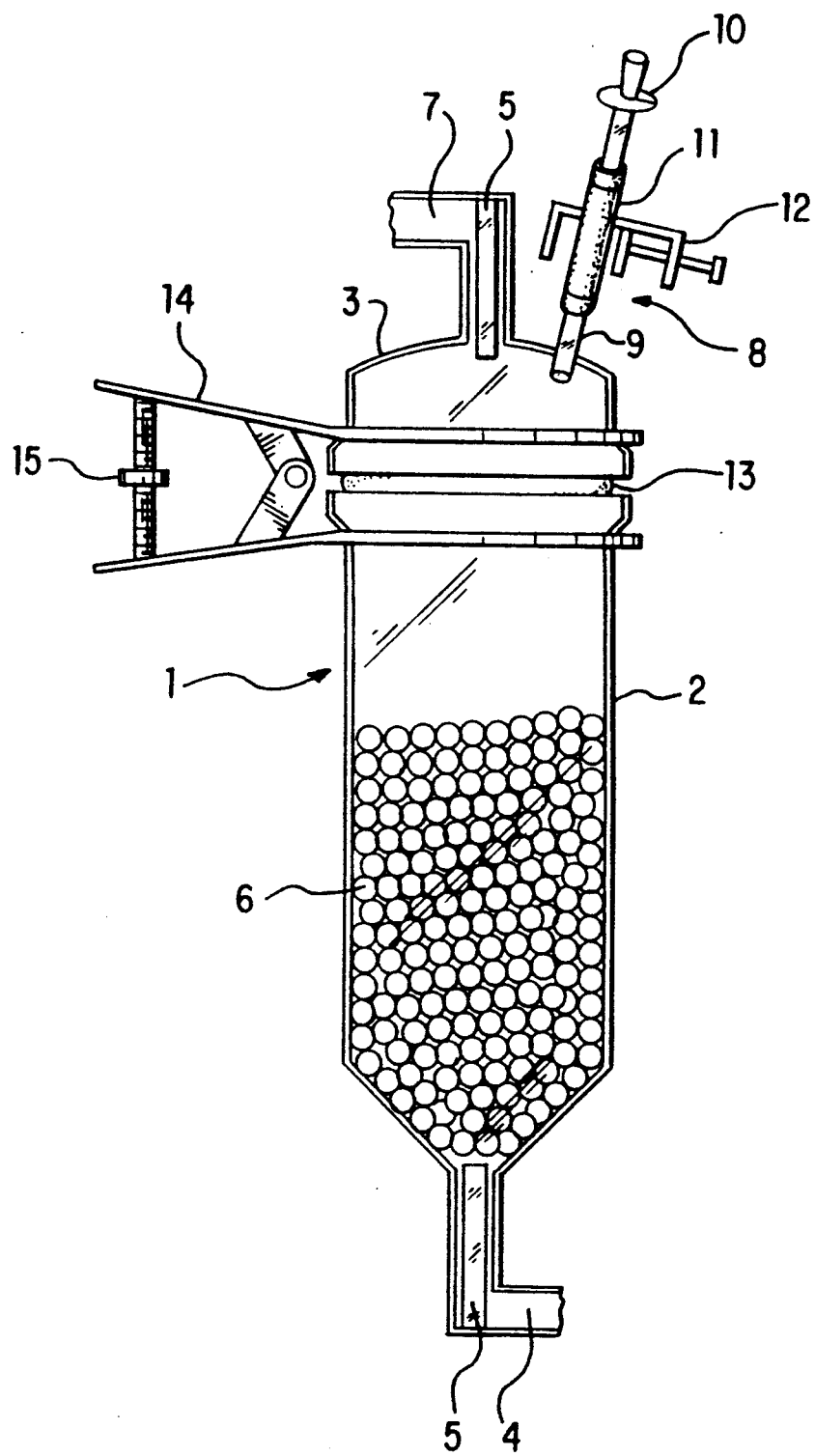
FIG. 1 is a diagrammatical sketch of the Hepatocyte Bioreactor described by the invention.

Referring to FIG. 1 there is shown a hepatocyte bioreactor which consists of a containment vessel (1) to house the support matrix (6) for entrapping hepatocyte aggregates. The containment vessel (1) is constructed with a glass bottom (2) and a lid (3). To the bottom (2) is attached a single L-shaped perfusion outlet (4) with a glass rod (5) fused into the vertical section serving to restrain the glass beads (6) which serves a matrix for the entrapment of hepatocyte aggregates. There is a L-shaped perfusion inlet (7) attached to lid (3) with glass rod (5) fused in the vertical section to serve as a restrainer for the glass beads (6). Also attached to the lid (3) is a cell injection port (8) consisting of a glass tube (9) fused into the lid (3) with a metal luer-lock fitting (10) attached to the glass tube (9) with a piece of rubber tubing (11). The injection port (8) can be closed using hose clamp (12). The bottom (2) and the lid (3) are held together and sealed using an O-ring (13) and O-ring glass joint clamp (14). The tension on the O-ring can be increased by turning tension adjustment knob (15). In the preferred embodiments glass has been used to make the bioreactor, matrix and other parts. However, other types of material can used so long as the material chosen does not interfere with function of the bioreactor or viability of the hepatocytes.

Manufacture and Use

The Containment vessel(l) has a bottom (2) and lid (3) which are made from standard matching O-ring glass joints. The inside diameter of the O-ring glass joints can be of any size. The bottom half needs to be of sufficient length to accommodate the volume of glass beads or matrix (6) required with a chosen inside diameter. The support matrix volume depends on the number of hepatocytes or aggregates thereof that are to be added. The hepatocytes density is at least $3 \times 10^6$ cells/ml but is near optimal at $6.70 \times 10^6$ cells/ml of matrix. The perfusion inlet (7) and perfusion outlet (4) are made from pyrex glass tubing. The glass rod bead retainers (5) must be of sufficient diameter so that the glass beads will not fit through the angular space between the glass rod (5) and the glass tubing (4) or (7). The luer-lock fitting (10) of the hepatocyte injection port (8) is made from stainless steel to allow for flame sterilization. The luer-lock fitting (10) is specifically machined to match standard plastic luerlock fittings. The matrix or beads (6) are made from Pyrex glass and can be of any size between 1 and 3 ml, with the size range 1.4 to 1.7 mm (between No. 14 and No. 12 mesh) being preferred for successful trapping of the hepatocyte aggregates. Other types of matrixes may be used to entrap hepatocyte aggregates besides glass beads. A successful matrix will be one that will entrap the hepatocytes or aggregates thereof while allowing perfusion.

Alternatively, the bottom (2) of the containment vessel can be made from standard glass tubing. A rubber stopper can be used as the lid (3) with the other features described above being manufactured in the same manner.

Figure 2:
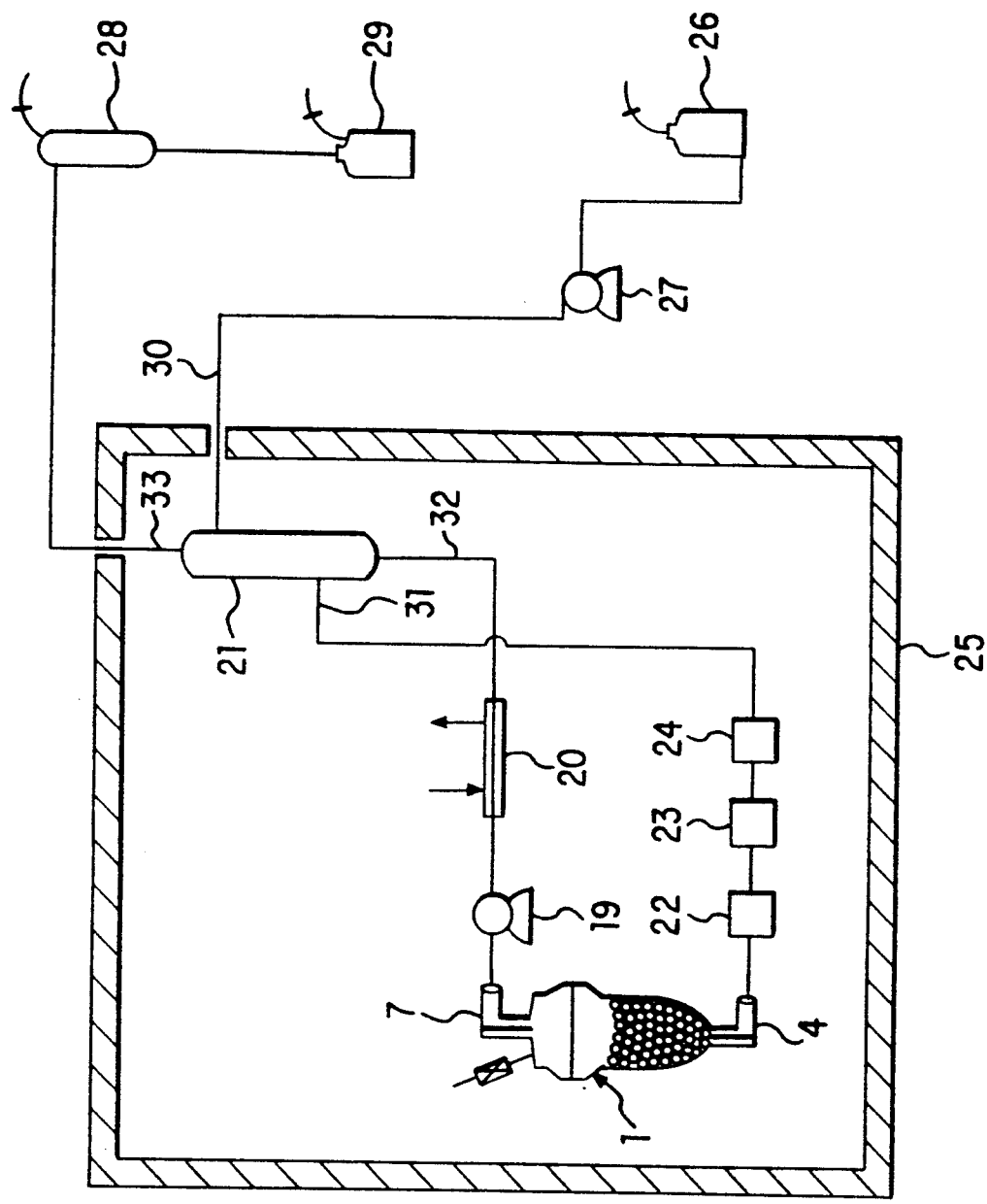
FIG. 2 is a flow diagram for the use of the Hepatocyte Bioreactor for metabolite production.

The previously described hepatocyte bioreactor [FIG (1)] can be used as a hepatocyte metabolism reactor when placed in a circuit shown in FIG. 2. The components are a recirculation peristaltic pump (19) and oxygenator (20), a degassing vessel (21), a pH probe (22), a dissolved oxygen probe (23), and an injection/sampling port (24). All these components are placed inside an incubator (25) held at a desired temperature preferably about 37° C. The fresh medium bottle (26), the feed pump (27), the product separation vessel (28), and the product collection bottle (29) are kept outside of the incubator (25).

The system is initially filled with fresh medium through line (30) from bottle (26) using feed pump (27). The media flows into the degassing vessel (21) until liquid level is above recycled return line (31). The recycle pump is activated so that the flow of the liquid follows a path through line (31), pass port (24) in probes (23) and (22) and fills containment vessel (1) from the bottom. The air is forced out of the system through the inlet port (7), through the oxygenator (20), into the vessel (21) through line (32). The air leaves the system through line (33) into vessel (28). Fresh medium is added until the system is totally liquid filled, the direction of the medium recycle is reversed with the medium now entering the containment vessel (1) through the inlet (7). Air is flowed through the annular oxygenator (20) in a countercurrent direction to the liquid flow. The initial oxygen composition should be close to that of air. Once the dissolved oxygen concentration is eqilibrated to that of air, the recycle pump (19) is turned off, and the hepatocytes or the hepatocyte aggregates thereof are injected into the system with a syringe to port (8). The displaced volume flows out of the system through line (33) into vessel (28). After the cells have been injected, the recycle pump (19) is turned on at a rate somewhat lower than the steady state recycle flow rate. The media and cells then recirculate through the system until the majority of the hepatocytes or the aggregates thereof have been entrapped within the glass beads. Fresh medium is then added to the system from vessel (26) through line (30) at a rate equivalent to 1 ml of media per day per one million cells entrapped.

Chemical compounds can be introduced in many different manners. In one mode they can be introduced as a constant composition feed in the fresh media in there is a need to further reduce the patient immunological response to the treatment. However, non-human hepatocytes can be used in the bioreactor as the hepatocyte aggregates. Since the patients' blood cells are prevented from coming into contact with the hepatocytes the immune response will be limited. Therefore, because of the availability, non-human hepatocytes are preferred, more preferably from cow, pig, goat or the like and most preferable from pig.

The medium used to support the hepatocyte bioreactor must contain the needed nutrients to maintain the viability of the hepatocytes or aggregates thereof. The medium may contain chemical agents that are being studied called substrates or chemicals formed from metabolism of the substrates called metabolites. When the hepatocyte bioreactor is being used as an extracorpeal support system the noncellular blood components of the mammals' blood can be used to provide the needed nutrients to support the hepatocyte aggregates in place of the medium.

The following examples are provided to illustrate the present invention and are not intended to limit the scope thereof. Those skilled in the art will readily understand that known variations of the conditions and processes of the following procedures can be used to practice the current invention.

EXAMPLES 1

Figure 4:
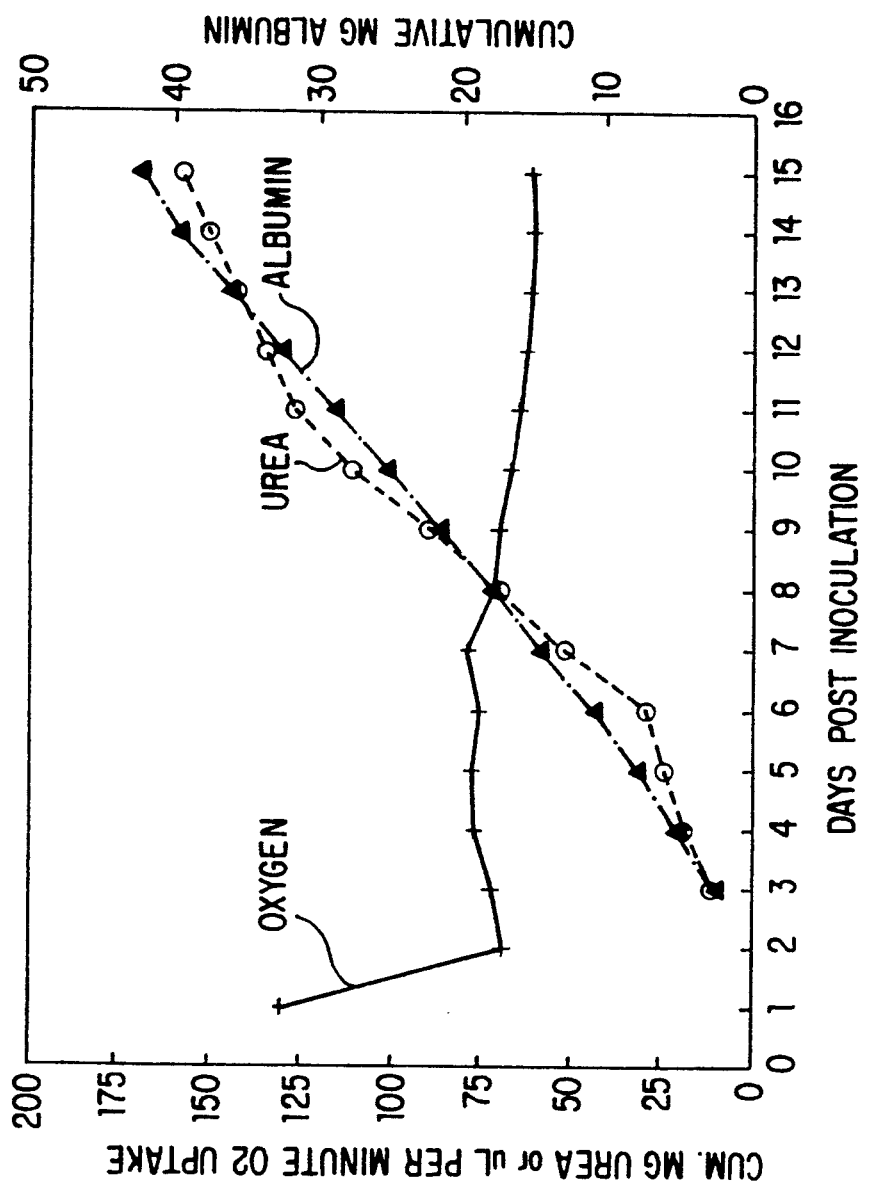
FIG. 4 is a graph showing representative data on indicators of viability.

Culturing of hepatocytes In the Hepatocyte Bioreactor (FIG. 1):

Hepatocytes were isolated from Sprague-Dawley rat using the biopsy procedure of Berry and Friend, 1969 "High-yield preparation of isolated rat liver parenchymal cells" *J. Cell Biol*, 43, 506–520, with some modifications (Loretz et al., "Promutagen activation by freshly isolated and cryopreserved rat hepatocytes", *Environ. Mol. Mutag.* 12:335–341; 1988; "Optimization of cryopreservation procedures for rat and human hepatocytes" *Xenobiotica* 19; 489–498; 1989), the disclosure of the above articles are hereby incorporated by reference. The procedure was a two-step collagenase (0.5% w/v, type I) perfusion technique. The isolated cell population routinely had over 80% viability as assessed by trypan blue exclusion. Following isolation, the hepatocytes were resuspended in Waymouth 752/L medium supplemented with 11.2 mg/l alanine, 12.8 mg/l serine, 24 mg/l asparagine, 2 g/l fatty acid poor bovine serum albumin, 0.168 mg/ml aminolevulinic acid, 5 mg/l oleic acid, 5 mg/l d,1-tocopherol, 0.393 mg/l dexamethasone, 7.9 mg/l d-thyroxine, 0.03 mg/l glucagon, 20 U./l insulin and 84 mg/l gentamicin (Green et al., Green, C. E., Segall, H. J.. and Byard, J. L. pg. 176–185 (1981)) Metabolism, cytotoxicity, and genotoxicity of the pyrrolizidine alkaloid senecionine in primary cultures of rat hepatocytes. *Toxicol. Appl. Pharmacol.* 60, 176). Cell density was adjusted to approximately $5 \times 10^6$ cells per ml. A total number of approximately $200 \times 10^6$ cells were inoculated into the bioreactor. For this number of cells, the bioreactor used had a dimension of 22 mm internal diameter and 83 mm height, containing approximately 30 ml of 1.5 mm diameter pyrex glass beads. The bioreactor was preequilibrated with the culture medium as described above for at least 24 hrs. prior to inoculation. The medium was recycled at a rate of 40 uls per minute. The total medium contained in the system was 150 ml. New medium as-added at a rate of approx. 200 ml per day. The system was maintained at 37 deg. C in a temperature-controlled incubator. The high viability of the hepatocyte cultured in the bioreactor was evidenced by the stable oxygen consumption, urea production, and albumin synthesis. Representative data on these indicators of viability are shown in FIG. 4. The major enzyme system responsible for drug metabolism, the P-450 mixed function oxygenase activity as measured by the ability of the hepatocyte to convert a chemical substrate, 7-ethoxycoumarin, to 7-OH-coumarin, for several studies is depicted in Table 1. Electron microscopy studies demonstrate that the cells in the aggregates have morphological characteristics of liver cells in vivo including bile canaliculi, peroxisomes, extensive endoplasmic reticulumn, tight cell junctions, and healthy mitochondria. Further, the aggregates in the matrix are interconnected via cell-cell contact. Hepatocyte cultured in the bioreactor in this fashion therefore are suitable for the studying of xenobiotic metabolism both for the evaluation of metabolic fate of xenobiotics (e.g. pharmaceutical) or for the massive production of metabolites. The system described here can also be used for the production of biological molecules known to be produced by the liver cells. The system can also be used to study chemical or drug toxicity.

TABLE 1

Metabolism of 7-Ethoxyycoumarin to 7-OH-coumarin by Hepatocyte Bioreactor

| Experiment | Hepatocytes | Days Post-inoculation | Production Rate (umoles per hour) |
|---|---|---|---|
| 1 | Rat, $200 \times 10^6$ | 5 | 3.8 |
| 2 | Rat, $200 \times 10^6$ | 5 | 5.2 |
| 3 | Rat, $200 \times 10^6$ | 7 | 4.9 |
| 4 | Rabbit, $200 \times 10^6$ | 3 | 1.6 |
|  |  | 8 | 0.6 |
| 5 | Rabbit, $200 \times 10^6$ | 10 | 0.5 |

EXAMPLE 2

Application of the bioreactor as an extracorporeal hepatic support system.

Figure 3:
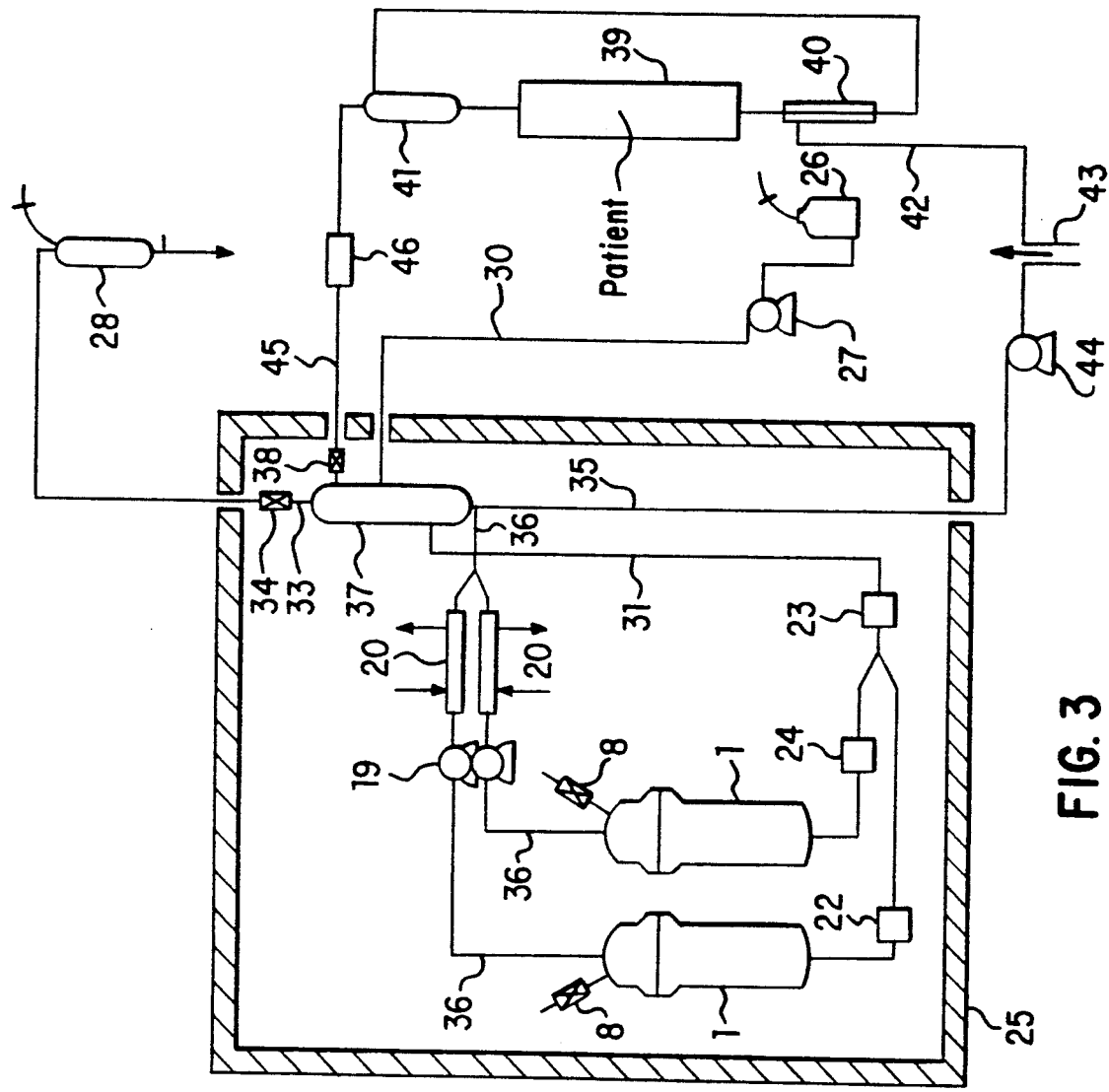
FIG. 3 is a flow diagram showing the FIG. 1 hepatocyte bioreactor connected to a patient in need of liver assistance.
Figure 5:
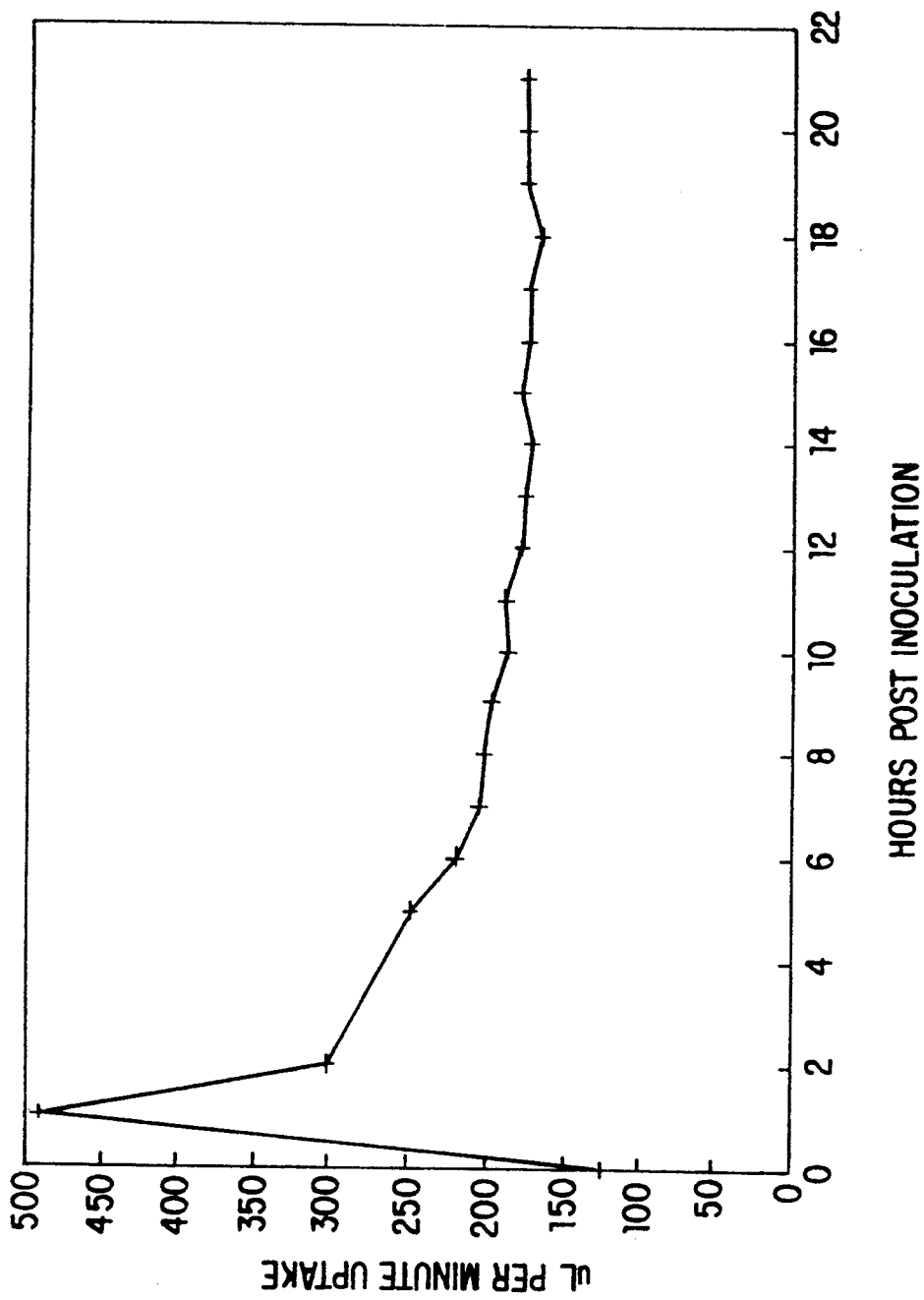
FIG. 5 shows hepatocytes oxygen consumption rate.

Hepatocytes were cultured from livers removed from an outbred Yorkshire/white pig using a procedure described in Example 1. From a pig liver, routinely 2 to 5 billion cells of high (over 80%) viability can be obtained. The medium used was the hormone-supplemented Waymouth medium as described in Example 1. To accommodate 2 to 5 billion cells, the bioreactor was scaled up to two containment vessels, each with an internal diameter of 40 mm and a height of 100 mm. Glass beads of approx. 2 mm diameter and a total volume of 250 ml per containment vessel were used. Medium was perfused at a recycle rate of 360 ml/min.. The high viability of the hepatocytes were evidenced by the stable oxygen consumption rate (FIG. 5). The bioreactor was attached to an ahepatic pig (liver removed by surgery to mimic total hepatic failure) at approx. 2 hrs. after hepatocyte inoculation. A schematic drawing of the application of the bioreactor as an extracorporeal hepatic support system is shown in FIG. 3. Blood from the left femoral artery was directed into a Minntech hemoconcentrator. A 12 fringe elecath canula was inserted into the femoral artery and connected to a ¼" PVC tubing to the hemoconcentrator. The hemoconcentrator separated the blood into a cell free ultrafiltrate fraction, and a blood cell fraction. The blood cell fraction was returned to the femoral vein via a similar tubing. The ultrafiltrate exited the hemoconcentrator via a ¼" PVC tubing and entered the hepatocyte bioreactor system with the flow rate adjusted to 40 ml/min. using bottle (26). Alternatively, they can be introduced as a bolus injection through injection port (24). Metabolic product can be collected in bottle (29), or reaction kinetics can be studied by taking samples through port (24). One skilled in the art can derive many different method to introduce chemicals into the hepatocyte bioreactor. The chemicals being introduced can be studied with respect to their interaction with hepatocytes, such as metabolic fate and toxicity or can be used as substrates for the synthesis of other compounds as metabolites.

The hepatocyte bioreactor (1) can also be used as an artificial organ supplying supplementary liver functioning to a patient in need thereof. In this mode, the hepatocyte bioreactor is arranged as shown in FIG. 3 to form a liver assist system for treating a mammal in need of liver assistance.

The hepatocyte bioreactor (1) can be considered as a modular unit and can be run in parallel with identical units to increase performance capacity. The requisite components for running the perfusion reactor in this mode are the same as the above with the following modifications:

The recycle pump (19) must be a multi-head peristaltic pump to insure equal flow of media through the individual perfusion reactors units (1); the degassing bottle (37) now also serves as a reservoir; a clamp (34) has been added to line (33) to keep liquid from exiting into vessel (28); the feed line (35) is introduced to inlet line (36) rather than into the degassing bottle (37). The system is initially filled with media from bottle (26) through line (30). During the filling period, clamp (34) is open, and clamp (38) is closed. When bottle (37) is filled with medium above recycle return line (31), the recycle pump (19) is activated and the system filled through line (31) displacing air through the top of the reactor (1) through the pump (19) and into the degassing bottle (37) through line (36). After the system has been totally medium filled, the media feed pump (27) is turned off and the direction of medium recycle reversed using pump (19). Air is added to the annular side of the oxygenator (20) with a composition equal to air. Once the medium is air saturated, the recycle pump is turned off and the hepatocytes or preformed aggregates thereof in the solution are added to the reactor(s) (1) through ports (8) using syringes. The recycle pump (19) is activated again and the cells and solution are allowed to recirculate through the system until most of the viable hepatocyte aggregates have been entrapped in the matrix or beads (6).

After the hepatocyte aggregates have had time to be entrapped, the system is flushed with fresh medium from bottle (26) to remove nonviable cells and other debris. After flushing is complete, clamp (34) is closed and clamp (38) is opened. Whole blood flows from the patient (39) through the hemoconcentrator (40) where liquid or plasma, called non cellular blood component or filtrate, is removed from the blood. This is done to minimize the immune response of the patient to the hepatocytes or aggregates thereof. The concentrated blood or blood cells exits the hemaconcentrator and is returned to the blood mixing vessel (41) where it is remixed with the filtrate exiting the bioreactor system or alternatively is directly reintroduced into the patient. The filtrate exits the hemoconcentrator (40) through line (42) and enters the filtrate reservoir/degassing bottle (43). Pump (44) is used to flow the filtrate from bottle (43) through line (35) to enter the system through line (36). The filtrate flows through the system, first passing through the oxygenator (20) into the containment vessel from the top, exiting the reactors from the bottom and returning to reservoir (37). A portion of the filtrate recycle flows into the reservoir (37), at a volume equal to the filtrate inlet flow through line (35), then exits the bioreactor circuit through line (45) passing through blood filter (46) before remixing with the concentrated blood in vessel (41) or is reintroduced directly into the patient.

The system can be generally viewed as consisting of two circuits. A hepatocyte bioreactor circuit and a patient side circuit. The two circuits are additionally connected by a reservoir (37) which receives the treated noncellular blood components from the hepatocyte bioreactor through line (31). It allows for a portion of the treated noncellular blood components to flow to the patient through line (45) and it also allows a portion to recycle back to the hepatocyte bioreactor through line (36). The reservoir (37) thereby allows for independent control over the flow rate of the blood in and out of the mammal and the flow rate of the noncellular blood components in and out of the hepatocyte bioreactor. This control over the two flow rates is preferred because different flow rates provide optimal performance of each circuit. The hepatocyte bioreactor needs a flow rate that is capable of providing adequate oxygen and nutrients with a minimum of shear damage to the hepatocytes. This flow rate may not be the same as the mammal's blood flow rate. Without further elaboration, one skilled in the art can, using the preceding description, utilize the present invention to its fullest extent. The following preferred specific embodiments are, therefore, to be construed as merely illustrative and not limitative of the remainder of the disclosure anyway whatsoever.

Formation of Cell Aggregates

Hepatocyte aggregates can be formed in two general fashions. By recycling hepatocytes through the bioreactor in cultured medium (see Example 1 for medium composition), the hepatocyte cells would contact each other and form aggregates, ultimately to a size that would be trapped by the matrix. We observed that in approximately 2-5 hours, approximately 50% of the hepatocyte would be trapped. In approximately 16-24 hours, approximately 100% of the cells would be trapped as aggregates.

Another mode to form hepatocyte aggregates is to form hepatocyte "spheroids" outside the bioreactor. The hepatocytes are placed in plastic or glass petri dish on a rotating platform in a $CO_2$ incubator (5% $CO_2$, 95% humidified air). Rotation of 30 cycles per minute is found effective. The hepatocyte would aggregate in approximately 24 hours. Such aggregates or spheroids, when passed through the bioreactor, would be trapped by the matrix.

After entrapment of the hepatocyte aggregates by either methods, the hepatocytes remain highly viable for an extended period (see Example 1). An important advantage of this invention is that the aggregates can form junctions with each other or become interconnected with each other, allowing cell-cell communication or contact among multiple hepatocyte aggregates. This three-dimension cell-cell contact and intercellular communication is similar to the liver in vivo.

Human hepatocytes work in the present invention and may be preferred in some situation. Like where a roller pump. After perfusion through the bioreactor, the ultrafiltrate was returned to the animal via the left jugular vein. To demonstrate the provision of extracorporeal hepatic metabolism, two different chemicals known to be metabolized by the liver, 7-ethoxycoumarin and lidocaine, were administered into the ultrafiltrate at the inlet of the bioreactor. The respective metabolites, 7-OH-coumarin and monoethylglycinexylidide (MEGX), were measured at the outlets of the bioreactors before the ultrafiltrate was returned to the animal. Significant metabolism of both 7-ethoxycoumarin and lidocaine were observed (FIGS. 6, 7 and 8). The results therefore demonstrate the application of the bioreactor as a support system, providing extracorporeal hepatic metabolism. This system can be used for the perfusion of human patients with hepatic failure. The separation of the blood cells from the plasma will minimize immunological reaction of the recipient to the hepatocyte. Hepatocytes from human donors (e.g. transplantable livers obtained from cadavers) and non-human source (such as pig) can be used in the bioreactor to provide extracorporeal hepatic support.

In addition to the variations and modifications of the apparatus suggested or described above, other variations and modifications will be apparent to those skilled in the art and, accordingly, the scope invention is not to be construed limited to the particular embodiments shown or suggested, but it is rather to be determined by reference to the appended claims.

What is claimed is:

1. A hepatocyte bioreactor, which comprises:
   a containment vessel having an inlet which allows hepatocytes or aggregates thereof to ingress into said containment vessel and an outlet which allows hepatocytes or aggregates thereof to egress;
   a matrix within said containment vessel into which said hepatocytes or aggregates thereof can ingress, said matrix being in fluid communication with said inlet and said outlet; and
   a plurality of hepatocyte aggregates entrapped within said matrix wherein said hepatocyte aggregates are interconnected within said matrix by cell-cell contact.

2. The hepatocyte bioreaction of claim 1 wherein said hepatocyte aggregates are spheroids.

3. The hepatocyte bioreactor of claim 1 wherein said matrix is glass beads.

4. The hepatocyte bioreactor of claim 1 wherein said hepatocyte aggregates are essentially free of connective tissue.

5. The hepatocyte bioreactor of claim 1 wherein said matrix has a hepatocytes density of at least about $3.00 \times 10^6$ cells per ml of matrix.

6. A method for making a bioreactor, which comprises the steps of:
   providing a containment vessel having an inlet which allows hepatocytes or aggregates thereof to ingress into said containment vessel and an outlet which allows hepatocytes or aggregates thereof to egress;
   providing a matrix within said containment vessel into which said hepatocytes or aggregates thereof can ingress, said matrix being in fluid communication with said inlet and said outlet; and
   entrapping a plurality of hepatocyte aggregates within said matrix wherein said hepatocyte aggregates are interconnected within said matrix by cell-cell contact.

7. The method for making a bioreactor as recited in claim 6 wherein said hepatocyte aggregates are spheroids.

8. The method for making a hepatocyte bioreactor of claim 6 wherein said matrix is glass beads.

9. The method for making a hepatocyte bioreactor of claim 6 wherein said hepatocyte aggregates are essentially free of connective tissue.

10. The method for making a heptocyte bioreactor of claim 6 wherein said matrix has a hepatocytes density of at least about $3.00 \times 10^6$ cells per ml of matrix.

11. The method for making a hepatocyte bioreactor of claim 6 wherein said hepatocyte aggregates are formed by perfusion of said hepatocytes through said matrix.

12. A method for using a hepatocyte bioreactor, which comprises the steps of:
    providing a containment vessel having an inlet which allows hepatocytes or aggregates thereof to ingress into said containment vessel and an outlet which allows hepatocytes or aggregates thereof to egress;
    providing a matrix within said containment vessel into which said hepatocytes or aggregates thereof can ingress, said matrix being in fluid communication with said inlet and said outlet;
    entrapping a plurality of hepatocyte aggregates within said containment vessel wherein said hepatocyte aggregates are interconnected within said matrix by cell-cell contact; and
    causing medium to be perfused through said inlet, said containment vessel and said outlet.

13. The method of using a hepatocyte bioreactor as recited in claim 12 wherein said plurality of hepatocyte aggregates are spheroids.

14. The method of using a hepatocyte bioreactor of claim 12 wherein said hepatocyte aggregates are formed by perfusion of said hepatocytes through said matrix.

15. The method of using a hepatocyte bioreactor as recited in claim 12 wherein said medium contains metabolites.

16. The hepatocyte bioreactor of claim 12 wherein said matrix is glass beads.

17. The method of using a hepatocyte bioreactor as recited in claim 12 wherein said hepatocyte aggregates are essentially free of connective tissue.

18. The method of using a hepatocyte bioreactor as recited in claim 12 wherein said matrix has a hepatocytes density of at least about $3.00 \times 10^6$ cells per ml of matrix.

19. A hepatocyte bioreactor liver assist system for treating a mammal in need of liver assistance, which comprises;
    means for extracting blood from the mammal in need of liver assistance;
    means for separating the blood of the mammal which is to be treated into cellular and non-cellular components;
    a hepatocyte bioreactor comprising; a containment vessel having an inlet which allows hepatocytes or aggregates thereof to ingress into said containment vessel and an outlet which allows hepatocytes or aggregates thereof to egress; a matrix within said containment vessel into which said hepatocytes or aggregates thereof can ingress; said matrix being in fluid communication with said inlet and aid outlet; and a plurality of hepatocyte aggregates entrapped within said matrix wherein said hepatocyte aggregates are interconnected within said matrix by cell-cell contact;

means causing said noncellular blood components of the mammal which is to be treated to be perfused through said inlet, said matrix and said outlet; and means to return said treated noncellular blood components and cellular blood components to said mammal.

20. The hepatocyte bioreactor liver assist system of claim 19 further comprising a means for maintaining a flow rate of medium through the hepatocyte bioreactor which is independent of the mammal.

21. The hepatocyte bioreactor liver assist system of claim 19 wherein said hepatocyte aggregates are spheroids.

22. The hepatocyte bioreactor liver assist system of claim 19 wherein said matrix is glass beads.

23. The hepatocyte bioreactor liver assist system of claim 19 wherein said hepatocyte aggregates are essentially free of connective tissue.

24. The hepatocyte bioreactor liver assist system of claim 19 wherein said matrix has a hepatocytes density of at least about $3.00 \times 10^6$ cells per ml of matrix.

* * * * *